(12) United States Patent  
Guichet

(10) Patent No.: US 8,992,527 B2  
(45) Date of Patent: Mar. 31, 2015

(54) ELONGATION NAIL FOR LONG BONE OR SIMILAR

(76) Inventor: Jean-Marc Guichet, Marseilles (FR)

( * ) Notice: Subject to any disclaimer, the term of this patent is extended or adjusted under 35 U.S.C. 154(b) by 103 days.

(21) Appl. No.: 13/378,784

(22) PCT Filed: Jun. 11, 2010

(86) PCT No.: PCT/FR2010/000429  
§ 371 (c)(1),  
(2), (4) Date: Mar. 7, 2012

(87) PCT Pub. No.: WO2010/149868  
PCT Pub. Date: Dec. 29, 2010

(65) Prior Publication Data  
US 2012/0165819 A1     Jun. 28, 2012

(30) Foreign Application Priority Data

Jun. 24, 2009   (FR) ..................................... 09 03051

(51) Int. Cl.  
*A61B 17/56* (2006.01)  
*A61B 17/58* (2006.01)  
*A61F 2/30* (2006.01)  
*A61B 17/72* (2006.01)

(52) U.S. Cl.  
CPC ................................. *A61B 17/7216* (2013.01)  
USPC ........................................................ 606/63

(58) Field of Classification Search  
USPC .................. 606/62–68, 53–60, 105  
See application file for complete search history.

(56) References Cited

U.S. PATENT DOCUMENTS

| | | | | |
|---|---|---|---|---|
| 5,074,882 A | * | 12/1991 | Grammont et al. | 606/63 |
| 5,263,955 A | * | 11/1993 | Baumgart et al. | 606/63 |
| 5,525,086 A | * | 6/1996 | Gentile et al. | 446/41 |
| 5,704,938 A | * | 1/1998 | Staehlin et al. | 606/62 |
| 5,704,939 A | * | 1/1998 | Justin | 606/63 |
| 5,720,746 A | | 2/1998 | Soubeiran | |
| 6,245,075 B1 | | 6/2001 | Betz | |
| 6,336,929 B1 | * | 1/2002 | Justin | 606/63 |

(Continued)

FOREIGN PATENT DOCUMENTS

| | | |
|---|---|---|
| EP | 0346247 A1 | 12/1989 |
| EP | 1477123 A1 | 11/2004 |

(Continued)

*Primary Examiner* — Mary Hoffman  
*Assistant Examiner* — Michelle C Eckman  
(74) *Attorney, Agent, or Firm* — Westerman, Hattori, Daniels & Adrian, LLP

(57) ABSTRACT

The present invention relates to elongation nails for long bones or similar. The elongation nail according to the invention is principally characterized in that it comprises a tube (10), another tube (20) mounted slidably and rotatably in the tube (10) in such a way that the end (21) of the tube (20) emerges from the end (11) of the tube (10), means (30) for coupling the two tubes (10, 20) in such a way that successive rotational oscillations of the two tubes with respect to each other about their longitudinal axis (100) cause a step-by-step translation of the two tubes with respect to each other. The nail also comprises an insert (40), mounted in a completely recessed position in the open end (12) of the first tube (10), and means (41) for locking the insert (40) with respect to the first tube, this insert having means (42) for cooperating with a lug of an ancillary instrument used to position the nail, said lug being able to be introduced into the end (12) of the tube (10) so as to cooperate with this insert (40).

10 Claims, 1 Drawing Sheet

(56) References Cited

U.S. PATENT DOCUMENTS

2002/0165544 A1* 11/2002 Perren et al. .................. 606/63
2009/0254088 A1* 10/2009 Soubeiran ..................... 606/63

FOREIGN PATENT DOCUMENTS

| WO | 9524870 A1 | 9/1995 |
| WO | 9615377 A1 | 5/1996 |

* cited by examiner

ELONGATION NAIL FOR LONG BONE OR SIMILAR

CROSS-REFERENCE TO RELATED APPLICATIONS

The present patent application is a nationalization of International application No. PCT/FR2010/000429, filed Jun. 11, 2010, published in French, which is based on, and claims priority from, French Application No. 0903051, filed Jun. 24, 2009, both of which are incorporated herein by reference in their entireties.

BACKGROUND OF THE INVENTION

1. Field of the Invention

The invention relates to the technical elements of prostheses mainly used in orthopedic surgery, particularly those known under the name of lengthening nails for long bone or similar.

We know that following malformations or congenital deficiencies or following fractures, loss of bone substance, or other, some bones such as humerus, femur, tibia, etc. are too short, creating an asymmetry or hypometry.

In the case of lower limbs, for a small discrepancy, below 3 cm, we can use insoles or orthopaedic shoes.

2. Description of Related Art Including Information Disclosed Under 37 CFR §§1.97 and 1.98

For a larger discrepancy or shortening, we can use, for a lengthening of the shorter limb, surgical solutions involving currently two methods, based respectively on external fixators or internal fixators.

In the technique based on external fixators, we use an external apparatus with some parts of it (e.g. metal wires) transfixing soft tissues to reach the bone to which they are secured. The apparatus is accessible from outside the limb, and the advantage of this technique is to allow the Practitioner to act on the apparatus at specified periods of time to induce in a gradual way some lengthening of the bone, generally at its diaphyseal level, after its section. However, these external fixators present mainly the following limitations: they are bulky and unsightly, patients in whom they are implanted sometimes cope with them with difficulty, and they result in significant risk of infection.

The technique based on internal fixators operates in a full internal way, i.e. no part is outside the limb. For this, we generally use nails called intramedullary nails or osteosynthesis plates properly fixed to the bone. The advantage of this solution with respect to the previous one lies in the fact that no device appears outside the limb. However, it is possible to obtain lengthening of the bone only through repeated surgical procedures, allowing, for each one, to obtain a fixed gain, limited by the elastic and plastic yield stresses on the soft tissues at stretching. In addition, in case of large non-gradual lengthening, the filling of the dimensional gap is inconstant and requires adjuvant means to the osteosynthesis, for instance bone grafts, which decrease the mechanical and physiological properties of the lengthened bone.

Technique of the Intramedullary Lengthening Nail

To overcome these drawbacks, the Applicant has made an original elongation nail (CAI), which was protected by patents, including EP 0,346,247. This achievement has as its goal to create a lengthening system combining the advantages of external fixators for a fully adjustable gradual lengthening, and benefits of internal fixators, without the drawbacks of both lengthening systems.

Other intramedullary lengthening nails have been made. For example, there is one that operates with rotations performed through maneuvers, which cannot be controlled with full security. The patient may over-lengthen in a very short time, which can lead to neurological complications or non-solidification of the bone.

Other intramedullary nails exist, like the one described in EP-A-1477123, which does not operate through rotation, but with two tubes which separate from one another translationally thanks to a part fixed into the pelvis, thus preventing hip motion.

Another, called 'electronic nail', is described in U.S. Pat. No. 6,245,075. It features an electric drive, which leads to security problems. Lack of charging during elongation has limited its clinical value.

We can also mention the intramedullary lengthening nail described in U.S. Pat. No. 5,704,939.

These lengthening systems according to the prior art have not diminished the qualities of the original elongation nail (CAI) mentioned above or its clinical interest, because they have some flaws, including lack of full weight bearing during the lengthening and operation with random failures.

Principle of Operation of the Initial Elongation Nail (CAI)

The original lengthening nail (CAI) according to the document mentioned above is remarkable as it is configured to fix at least two parts of the same bone, sectioned into two parts, and it is made of parts able to confer a gradual lengthening, resulting from a partial rotation applied by external maneuvers on the limb concerned, and/or acquired automatically during physiological motion of the limb, for instance while walking, and it is also made of parts for maintaining the obtained lengthening after each rotation applied on the limb and the neutral rotation of bone segments of the limb concerned.

This nail mainly comprises a sleeve within which is mounted, with translational displacement capacity, a tube with suitable means adapted to cause relative displacement of the sleeve and the tube as a result of rotational movements applied to the limb in one direction corresponding to a lengthening of the bone, and in the other direction of rotation to achieve the blocking of the translation of the tube with respect to the sleeve. Translation is obtained by means of ratchet teeth.

BRIEF SUMMARY OF THE INVENTION

The present invention aims in particular to enhance structurally the CAI nail and its operation, to optimize clinical outcomes, to reduce ratcheting which is sometimes difficult or painful, to improve the limited weight bearing during the lengthening period, to decrease difficulties positioning of the two tubes, to decrease difficulties in its removal in case it is fully buried inside the bone, and to allow it to cooperate with the same ancillary instrument whatever the size of the lengthening nail.

More specifically, this invention relates to a lengthening nail for long bone or similar, comprising:
  a first hollow tube with an inner diameter of a first value, a second tube with an outer diameter of a second value at most equal to the first value, said second tube being mounted to slide and rotate in said first tube so that a first of the ends emerges from a first of the two ends of the first tube, and
  means for coupling the first and second tubes in a way that successive alternating rotations of the two tubes with respect to the other one around their longitudinal axis result in a longitudinal step by step translation of the two tubes, in relation to one another, characterized by the fact that the second end of the first tube is open, and that the said nail further includes a ferrule mounted fully embedded in said second end of the first tube, and means for locking said ferrule with respect to the said first tube, said ferrule having means for cooperating with a lug of an ancillary instrument for setting of the nail, said lug being adapted to be inserted in the second end of the first tube to cooperate with said ferrule.

BRIEF DESCRIPTION OF THE SEVERAL VIEWS OF THE DRAWINGS

Other features and advantages of the present invention will become apparent from the following description, with reference to the accompanying drawings provided for illustration, but not limiting, wherein.

DETAILED DESCRIPTION OF THE INVENTION

Figure 1:
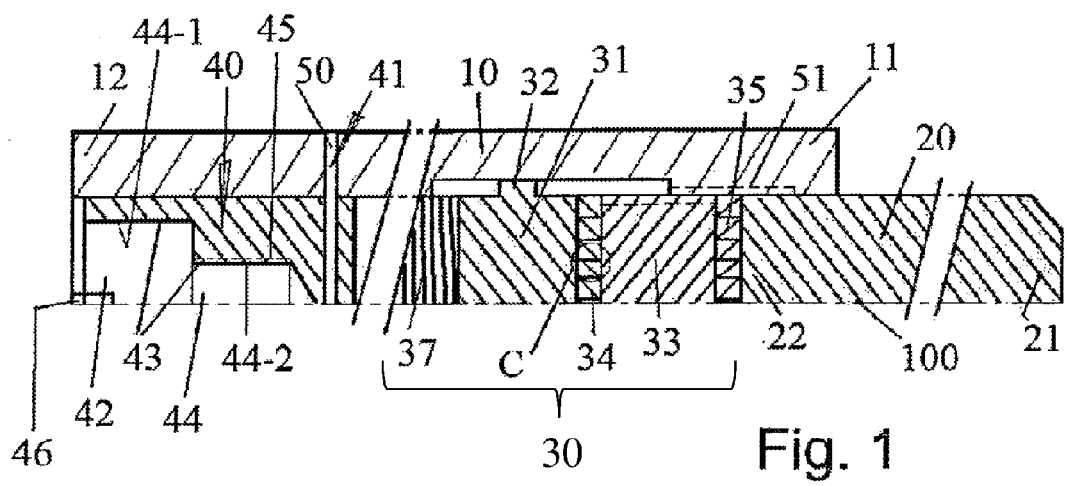
FIG. 1 is a partial longitudinal section of an embodiment of the lengthening nail according to the invention.

The present invention relates to an intramedullary lengthening nail for long bone or similar, of similar type as the one defined in the prior document EP-A-0346247 mentioned in the preamble to the present description.

The lengthening nail according to the invention includes a first hollow tube 10 with an inner diameter of a first value, a second tube 20 with an outer diameter of a second value at most equal to the first value, this second tube, hollow or not, but preferably solid and cylindrical or reasons of strength, being mounted to slide and rotate in the first tube 10 so that a first 21 of its two ends emerges from a first 11 of the two ends of the first tube 10, and means 30 for coupling the first and second tubes 10, 20 so that successive alternating rotations of the two tubes in relation to one another around their longitudinal axis 100 result in a longitudinal, step-by-step translation of the two tubes one with respect to the other.

An embodiment of the means 30 for coupling the two tubes according to the aims defined above, will be given below, consistent with the structure described in EP-A-0346247.

In an essential feature of the invention, as illustrated in FIG. 1, the second end 12 of the first tube 10 is open, and the nail includes a ferrule mounted, preferably fully embedded, in this second end 12 of the first tube 10, and means 41 for locking the ferrule 40 with respect to the first tube. These means 41 to lock the ferrule comprise at least one pin 50, or equivalent system, passing through at least a portion of the wall of the first tube 10 and at least a portion of the wall of the ferrule 40, as shown in FIG. 1.

According to another key feature of the invention, the ferrule 40 includes means 42 for cooperating with a lug of the ancillary instrument for setting the nail (not shown) so that this lug can be introduced in the second end 12 of tube 10 to cooperate with the ferrule 40, for example by plugging.

Advantageously, the means for cooperating 42 are comprised of one 43 of the two parts of a male-female joint.

Preferably, this part 43 of the male-female joint is the female part 44, in a way that there is no element protruding from the lateral wall of tube 10, like a pin or similar, nor a cavity, in order to avoid, after implantation of the first tube into the bone, the formation of ossification around the pin or in the cavity, which would prevent extraction of the nail from the bone.

However, this ferrule 40 fully inserted into the end 12 of the first tube 10, will facilitate the extraction of the nail when the desired value of lengthening of the bone will be obtained, mainly thanks to the female part 44 cooperating with a male part of the lug of the ancillary instrument.

Furthermore, for a secure implantation of the lengthening nail, it is advantageous that this female part 44 includes, as shown in FIG. 1, at least two consecutive female portions 44-1, 44-2 along the longitudinal axis 100 defined above.

These two consecutive female portions 44-1, 44-2 have different cross sections, the cross section of the female portion 44-1 closest to the second end 12 of the first tube 10 being greater than that of the other female portion 44-2.

They are therefore advantageously comprised of two substantially cylindrical chambers, the inner wall of the chamber 44-1 closest to the second end 12 of the first tube 10 being substantially smooth to form a guide, the inner wall of the second chamber 44-2 having a mounting thread 45.

The lengthening nail also includes means 46 for indexing the lug of the ancillary instrument with respect to the first hollow tube 10 and/or to the ferrule 40, since this ferrule 40 and the first tube 10 are fixed with respect to each other, in order to facilitate the positioning of the lug of this ancillary instrument and of the nail with respect to the bone to be lengthened. These indexing means may be formed, as shown in FIG. 1, by a notch formed in the inner wall of the first tube 10 and/or in the ferrule 40.

As to the means 30 for coupling the first tube 10 to the second tube 20, in a way that the alternating rotations of these two tubes with respect to one another one result in a step-by-step longitudinal translation of one tube with respect to one another, they include advantageously, as shown in FIG. 1, at least one plug 31 slidingly mounted in the first tube 10 between the insert 40 and the second end 22 of the second tube 20, means 32 for preventing this plug 31 from rotating on itself in the first tube 10, a threaded socket 33 screwed into a complementary thread 51 formed in the inner wall of the first tube 10, this threaded socket 33 being disposed between the plug 31 and the second end 22 of the second tube 20, two complementary pairs of ratchet bosses 34 and 35 with teeth 36 having a substantially saw tooth form, these two pairs of ratchet bosses 34, 35 being mounted respectively in cooperation between the plug 31 and the threaded socket 33, and between the threaded socket 33 and the second end 22 of second tube 20, each pair of ratchet bosses having the opposite direction of rotation, and compensating spring means 37 for absorbing the relative separation of the three elements: plug 31, threaded socket 33 and second tube 20, when the teeth 36 of a given pair 34, 35 move past each other. As will be appreciated from FIG. 1, the pairs of ratchet bosses 34 and 35 are coaxial about the axis 100; and the pair of ratchet bosses 34 is symmetric with the pair of ratchet bosses 35 about a plane equidistant between them, perpendicular to the axis 100.

Figure 2:
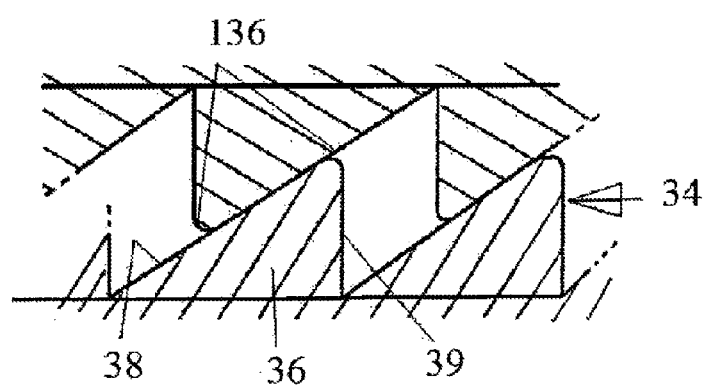
FIG. 2 is a schematic sectional view of a detail of the embodiment according to FIG. 1, circled as 'C' in FIG. 1.

According to a preferred embodiment, to facilitate moving of the teeth past each other, as shown in FIG. 2 which shows at a larger scale the circled portion C referenced in FIG. 1, each tooth 36 has an oblique slope 38 and a right slope 39 joined at a vertex 136 that has a strongly rounded shape.

In an advantageous way, and which has given full satisfaction to the Applicant, at least one pair of ratchet bosses, preferably two pairs, includes two opposed pair of about twenty-four teeth. This latter feature improves the quality of clinical rotational maneuvers and increases the mechanical properties of the nail according to the invention by allowing a further reduction in overall size dimensions of the elements respectively referenced 10, 20, 30 and 40.

The functioning of the lengthening nail according to the invention is the same as the one described in the earlier document EP-A-0 346 247 mentioned above. It will not be further addressed here.

However, it is useful to mention here the benefits of the nail according to the present invention, which are consequences of the structural improvements compared to the original lengthening nail (CAI).

Among them, we can note:

facilitation of positioning of the nail and of its extraction with its ferrule 40 with a dual escapement and inner thread, even when the nail is buried in the bone and new bone formation, elimination of cavities on the surface of the tube 10, thus avoiding ossification complicating extraction of the nail, change in morphology of the ratchet bosses increasing safety and allowing for smaller diameters of nails, and facilitation of ratcheting, better control over ratcheting maneuvers with a potential decrease of pain.

The invention claimed is:

1. An elongation nail for a bone, including a long bone, comprising:

a first hollow tube (10) having open first and second ends (11, 12) and an inner diameter of a first value, a second tube (20) having first and second ends (21, 22) and an outer diameter of a second value at most equal to the first value, the second tube having a common longitudinal axis (100) with the first tube and being slidably and rotatably mounted in the first tube (10) with the first end (21) of the second tube emerging from the first end (11) of the first tube (10), a coupling (30) for coupling the first and second tubes (10, 20) to each other so that successive alternating rotations of the first and second tubes in relation to one another about the common longitudinal axis (100) result in a longitudinal step-by-step translation of the first and second tubes in relation to one another, a ferrule (40) mounted completely inserted in the second end (12) of the first tube, the ferrule having an inner end facing the coupling, an outer end facing the second end of the first tube, and a cavity extending inwardly from the outer end, the cavity having a longitudinal axis coinciding with the common longitudinal axis (100) of the first and second tubes and defining a female part for cooperation (42) with a male lug of an ancillary tool for setting of the nail, the lug being adapted to be inserted into the second end (12) of the first tube (10) to cooperate with the female part of the ferrule (40) to form a male-female joint, wherein the cavity has two consecutive, cylindrical female portions (44-1, 44-2) having cylindrical walls with cross-sections of different sizes from each other along the longitudinal axis (100), and means (41) for fixing the ferrule (40) with respect to the first tube.

2. The nail according to claim 1, wherein the cross section of the cylindrical female portion (44-1) closest to the second end (12) of the first tube (10) is larger than the cross-section of the other cylindrical female portion (44-2).

3. The nail according to claim 2, wherein the wall of the female portion nearest (44-1) the second end (12) of the first tube (10) being substantially smooth to form a guide, the wall of the other female portion (44-2) having a mounting thread (45).

4. The nail according to claim 1, wherein the means (41) for fixing the ferrule (40) in relation to the first tube (10) comprise at least one pin (50) through both at least part the first tube (10) and at least part of the ferrule (40).

5. The nail according to claim 1, further comprising a notch formed in at least one of the inner wall of the first tube (10) and the ferrule (40) for indexing the lug of an ancillary instrument from at least one of the first hollow tube (10) and the ferrule (40).

6. An elongation nail for a bone, including a long bone, comprising:

a first hollow tube (10) having open first and second ends (11, 12) and an inner diameter of a first value, wherein the first tube (10) has an inner wall;

a second tube (20) having first and second ends (21, 22) and an outer diameter of a second value at most equal to the first value, the second tube having a common longitudinal axis (100) with the first tube and being slidably and rotatable mounted in the first tube (10) with the first end (21) of the second tube emerging from the first end (11) of the first tube (10);

a coupling (30) for coupling the first and second tubes (10, 20) to each other so that successive alternating rotations of the first and second tubes in relation to one another about the common longitudinal axis (100) result in a longitudinal step-by-step translation of the first and second tubes in relation to one another, wherein the coupling (30) comprises at least:

a plug (31) slidably mounted in the first tube (10) between the ferrule (40) and the second end (22) of the second tube (20), means (32) for preventing the plug (31) from being rotated on itself in the first tube (10), a threaded socket (33) rotatably mounted in a complementary thread screw (51) formed on the inner wall of the first tube (10), the threaded socket being disposed between the plug (31) and the second end (22) of the second tube (20), first and second pairs of complementary ratchet bosses (34, 35) with teeth (36) having a substantially sawtooth form, the first pair (34) of the first and second pairs of ratchet bosses (34, 35) being mounted in cooperation between the plug (31) and the threaded socket (33) coaxial with the longitudinal axis (100), and the second pair (35) of the first and second pairs of ratchet bosses being mounted in cooperation between the threaded socket (33) and the second end (22) of second tube (20) coaxial with the longitudinal axis (100), the ratchet bosses of each pair of ratchet bosses having opposite directions of rotation, and a compensating spring (37) for absorbing the relative separation of the plug (31), the threaded socket and the second tube, when the teeth (36) of either pair of ratchet bosses (34, 35) move past each other;

a ferrule (40) mounted completely inserted in the second end (12) of the first tube, the ferrule having an inner end facing the coupling, an outer end facing the second end of the first tube, and a cavity extending inwardly from the outer end, the cavity having a longitudinal axis coinciding with the common longitudinal axis (100) of the first and second tubes and defining a female part for cooperation (42) with a male lug of an ancillary tool for setting of the nail, the lug being adapted to be inserted into the second end (12) of the first tube (10) to cooperate with the female part of the ferrule (40) to form a male-female joint, wherein the cavity has two consecutive, cylindrical female portions (44-1, 44-2) having cylindrical walls with cross-sections of different sizes from each other along the longitudinal axis (100), and means (41) for fixing the ferrule (40) with respect to the first tube.

7. The nail according to claim 6, wherein each tooth (36) has an oblique slope (38) and a right slope (39) joining at a vertex (136), the vertex being highly rounded in shape to facilitate passage of the teeth past each other.

8. The nail according to claim 7, wherein the at least one of the pairs of ratchet bosses are two pairs of about twenty-four teeth.

9. The nail according to claim 6, wherein the at least one of the pairs of ratchet bosses are two pairs of about twenty-four teeth.

10. The nail according to claim 6, wherein the first pair of ratchet bosses (34) is symmetric with the second pair of ratchet bosses (35) about a plane equidistant between them, perpendicular to the longitudinal axis (100).

* * * * *